United States Patent [19]

Takefumi et al.

[11] Patent Number: 5,208,383
[45] Date of Patent: May 4, 1993

[54] PROCESS FOR PRODUCING AROMATIC ACYLATION PRODUCT

[75] Inventors: Tadayoshi Takefumi; Yoshihiro Shiokawa; Shunichi Matsumoto; Nobuyuki Tokura, all of Kurashiki, Japan

[73] Assignee: Mitsubishi Gas Chemical Company, Inc., Tokyo, Japan

[21] Appl. No.: 825,275

[22] Filed: Jan. 24, 1992

Related U.S. Application Data

[63] Continuation-in-part of Ser. No. 737,231, Jul. 29, 1991, abandoned.

[30] Foreign Application Priority Data

Jun. 14, 1991 [JP] Japan ............................. 3-169005

[51] Int. Cl.$^5$ ............................................. C07C 45/45
[52] U.S. Cl. ..................................... 568/323; 562/848; 568/322
[58] Field of Search ................... 568/323, 322; 562/848

[56] References Cited

U.S. PATENT DOCUMENTS

| | | | |
|---|---|---|---|
| 3,962,343 | 6/1976 | Fujiyama et al. | 260/599 |
| 4,967,011 | 10/1990 | Tokura et al. | 568/323 |

FOREIGN PATENT DOCUMENTS

| | | | |
|---|---|---|---|
| 84742 | 8/1983 | European Pat. Off. | 568/323 |
| 0199661 | 10/1986 | European Pat. Off. | 45/46 |
| 0202403 | 11/1986 | European Pat. Off. | 45/46 |
| 0203276 | 12/1986 | European Pat. Off. | 45/46 |
| 0215351 | 3/1987 | European Pat. Off. | 45/46 |
| 0361479 | 4/1990 | European Pat. Off. | 45/46 |
| 3213395 | 10/1983 | Fed. Rep. of Germany | 568/323 |
| 60-188343 | 9/1985 | Japan | 568/323 |
| 61-243042 | 10/1986 | Japan | 568/323 |
| 61-271243 | 12/1986 | Japan | 568/323 |
| 61-277643 | 12/1986 | Japan | 568/323 |

OTHER PUBLICATIONS

Patent Abstracts of Japan vol. 10 No. 36 (C-328) [2093] Feb. 13, 1986, (Kokai 60-188 343).
Patent Abstracts of Japan vol. 12 No. 358 (C531) [3205] Sep. 26, 1988, (Kokai 63-115 843).
Yasui et al., Chem. Abst., vol. 92, No. 215,144K (1980).
Takefumi et al., Chem. Abst., vol. 109, No. 128,384q (1988).

*Primary Examiner*—James H. Reamer
*Attorney, Agent, or Firm*—Wenderoth, Lind & Ponack

[57] ABSTRACT

A process for producing an aromatic acylation product from an aromatic compound, an olefin and carbon monoxide, which comprises the steps of:

(a) reacting an olefin with carbon monoxide in the presence of hydrogen fluoride and boron trifluoride at a pressure of not more than 100 kg/cm$^2$G to prepare an acyl fluoride synthesis solution, (b) allowing the acyl fluoride synthesis solution to absorb boron trifluoride to form a complex of acyl fluoride and boron trifluoride, (c) subjecting an aromatic compound to an acylation reaction with a reaction mixture containing the complex of acyl fluoride and boron trifluoride, obtained in the step (b), to form a complex of boron trifluoride, hydrogen fluoride and an aromatic acylation compound, provided that the amount of the acyl fluoride in the complex of acyl fluoride and boron trifluoride is less than 1 mole per mole of the aromatic compound, and (d) separating the aromatic acylation compound from the complex formed in the step (c) by heating a reaction mixture obtained in the step (c).

14 Claims, 1 Drawing Sheet

I # PROCESS FOR PRODUCING AROMATIC ACYLATION PRODUCT

This application is a continuation-in-part of now abandoned application Ser. No. 07/737,231 filed Jul. 29, 1991.

FIELD OF THE INVENTION

The present invention relates to a process for producing an aromatic acylation product, which comprises reacting an aromatic compound, an olefin and carbon monoxide.

DESCRIPTION OF RELATED PRIOR ART.

A process for acylating an aromatic compound with acid fluoride in the presence of hydrogen fluoride (HF) and boron trifluoride ($BF_3$) is known. That is, Japanese Laid-open Patent Publication No. 135756/1979 discloses a process for producing 2-alkyl-6-acylnaphthalene, in which 2-alkylnaphthalene is reacted with an acylating agent in the presence of $BF_3$ or a combination of HF and $BF_3$. EP-A-0215351 discloses a process for producing an aromatic acylation product from an aromatic compound in which an acid anhydride is preliminarily reacted with HF to synthesize acyl fluoride and the aromatic compound is acylated with the acyl fluoride. Japanese Laid-open Patent Publication No. 115843/1988 discloses a process for producing isobutyryl fluoride, in which propylene and carbon monoxide are reacted in the presence of HF and $BF_3$. U.S. Pat. No. 4,967,011 describes a process in which a specific mixed solvent is used when an aromatic acylation product is separated from a complex composed of HF-$BF_3$ and an aromatic acylation compound by heating an acylation reaction solution obtained.

As shown in the above prior art documents, these conventional processes for producing an aromatic acylation product comprise reacting an olefin with carbon monoxide in the presence of HF and $BF_3$ to synthesize an acyl fluoride and then reacting the acyl fluoride with an aromatic compound in the presence of HF and $BF_3$. In these processes, a side reaction takes place between an unreacted olefin and an aromatic compound. It is hence difficult to increase the yield of the aromatic acylation product. Further, the acyl fluoride is synthesized under a pressure of 20 kg/cm$^2$G or higher in order to increase the reaction rate of carbon monoxide and the acylation is carried out in an acylation reactor set at a pressure of 10 kg/cm$^2$G or lower, generally under a pressure of 5 kg/cm$^2$G or lower. As a result, carbon monoxide dissolved in the synthesis liquid of the acyl fluoride and nitrogen and hydrocarbon gas being present in the starting materials are released as a gas due to the pressure reduction in the acylation reactor, and $BF_3$ is taken out together with the above gas. In order to prevent the discharge of the release $BF_3$ into atmosphere, for example, one means is taken in which $BF_3$ is absorbed by an alkaline solution. In this case, however, an effluent of the alkaline solution contains a higher concentration of $BF_3$. Therefore, when such a reactor using HF and $BF_3$ as a catalyst is used, it is required to take severe environmental protection means, and it is desired to add an effective improvement to the reaction process.

SUMMARY OF THE INVENTION

It is an object of the present invention to provide a process for producing an aromatic acylation product in excellent yields.

It is another object of the present invention to provide a process for producing an aromatic acylation product, in which boron trifluoride released from the acylation reaction of an aromatic compound can be efficiently utilized.

It is further another object of the present invention to provide a process for producing an aromatic acylation product, in which the discharge of boron trifluoride released from the acylation reaction of an aromatic compound into atmosphere can be prevented without taking means of the absorption with an alkali solution, etc.

According to the present invention, there is provided a process for producing an aromatic acylation product from an aromatic compound, an olefin and carbon monoxide, which comprises the steps of:

(a) reacting an olefin with carbon monoxide in the presence of hydrogen fluoride and boron trifluoride at a pressure of not more than 100 kg/cm$^2$G to prepare an acyl fluoride synthesis solution, (b) allowing the acyl fluoride synthesis solution to absorb boron trifluoride to form a complex of acyl fluoride and boron trifluoride, (c) subjecting an aromatic compound to an acylation reaction with a reaction mixture containing the complex of acyl fluoride and boron trifluoride, obtained in the step (b), to form a complex of boron trifluoride, hydrogen fluoride and an aromatic acylation compound, provided that the amount of the acyl fluoride in the complex of acyl fluoride and boron trifluoride is less than 1 mole per mole of the aromatic compound, and (d) separating the aromatic acylation compound from the complex formed in the step (c) by heating a reaction mixture obtained in the step (c).

DETAILED DESCRIPTION OF THE INVENTION

Figure 1:
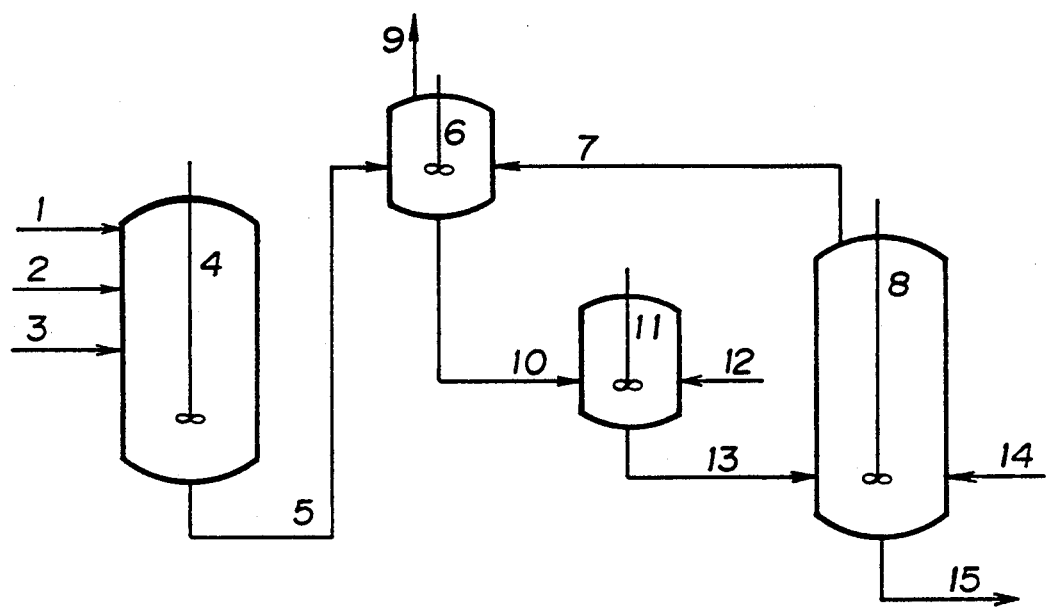
FIG. 1 is a flow chart showing one embodiment of the production of an aromatic acylation product according to the process of the present invention.

The present inventors have diligently studied the above process for producing an aromatic acylation product in which an olefin is reacted with carbon monoxide in the presence of HF and $BF_3$ to prepare an acyl fluoride, and the acyl fluoride is reacted with an aromatic compound. As a result, it has been found that an aromatic compound. As a result, it has been found that an aromatic acylation product can be produced in high yields by preliminarily allowing acyl fluoride synthesis solution to absorb $BF_3$ and then subjecting an aromatic compound to an acylation reaction with the acyl fluoride synthesis solution. It has been further found that the yields of an aromatic acylation product can be even further increased by bringing a gas released as $BF_3$ during the acylation reaction into contact with the acyl fluoride synthesis solution, and that the discharge of $BF_3$ in a released gas into atmosphere can be prevented by contacting the released gas with the acyl fluoride synthesis solution or with the aromatic compound as a starting material. The above objects and advantages of the present invention will be apparent from the following description.

The aromatic compound used as a starting material in the present invention includes alkylbenzene compounds such as toluene, xylene, trimethylbenzene, ethylbenzene, cumene, butylbenzene, etc.; alkylnaphthalene compounds such as naphthalene, methylnaphthalene, ethylenaphthalene, etc.; phenolic compounds; naphthol compounds; and aromatic ether compounds such as anisole, phenyl ether, etc.

The olefin used to produce an acyl fluoride as an acylating agent is selected from olefins having 2 to 5 carbon atoms such as ethylene, propylene, butylene, isobutylene, pentene, etc.

In the present invention, at first, the olefin and carbon monoxide are reacted with each other in a reactor to synthesize an acyl fluoride.

The above reaction is carried out at a pressure of not more than 100 kg/cm$^2$G, preferably at a pressure of 20 to 80 kg/cm$^2$G. When this pressure is lower than 20 kg/cm$^2$G, the reaction rate is low. Even when it is higher than 80 kg/cm$^2$G, there is not any further increase in the yield of the acyl fluoride, and the cost for an apparatus increases comparatively. The reaction temperature is in the range between 5° C. and 70° C., preferably between 20° C. and 50° C. When the reaction temperature is too low, the synthesis takes too long a time. When this temperature is too high, the yield decreases.

In the reaction for the synthesis of the acyl fluoride, the amount of HF for use per mole of the olefin is 5 to 20 moles, preferably 7 to 15 moles. The amount of BF$_3$ for use per mole of HF is 0.001 to 0.03 mole, preferably 0.005 to 0.02. Even if the amount of BF$_3$ is larger, or even if it is smaller, than the above range, the yield decreases. The optimum amount of BF$_3$ is within the above range.

From the reactor for the synthesis of the acyl fluoride, a hydrogen fluoride solution of acyl fluoride is obtained after the reaction under the above conditions. The hydrogen fluoride solution of acyl fluoride is allowed to absorb BF$_3$, whereby a complex of acyl fluoride and BF$_3$ is formed. This complex and the aromatic compound are subjected to an acylation reaction in the presence of hydrogen fluoride and boron trifluoride, whereby a complex of the aromatic compound and HF-BF$_3$ is obtained. The aromatic acylation product is recovered by decomposing the complex under heat and separating HF and BF$_3$.

The amount of the acyl fluoride for use per mole of the aromatic compound is less than 1.0 moles, preferably 0.8 to 1.0 mole (exclusive). When the amount of the acyl fluoride is 1.0 mole or more, the acyl fluoride reacts with a solvent such as benzene, toluene, etc., used for recovering the aromatic acylation product by decomposing the complex under heat and separating hydrogen fluoride and boron trifluoride. As a result, disadvantageously, there is a loss in the solvent and the acyl fluoride. When the amount of the acyl fluoride is less than 1 mole, part of the aromatic compound remains unreacted. However, the remaining aromatic compound can be easily recovered by separating it from the aromatic acylation product, e.g., by distillation. The recovered aromatic compound can be recycled. The amount of the boron trifluoride for use per mole of the aromatic compound is 1.5 to 3.0 moles, preferably 1.8 to 2.5 moles. The amount of the hydrogen fluoride for use per mole of the aromatic compound is 5 to 20 moles, preferably 7 to 15 moles. In general, the hydrogen fluoride contained in the acyl fluoride synthesis solution is directly used as such for the acylation reaction.

The acylation temperature is in the range of between −20° C. and 30° C., preferably between −10° C. and 20° C. When this temperature is elevated, the reaction rate increases. At the same time, however, the side reaction rate also increases. As a result, the amount of by-products increases. It is necessary to take into consideration the melting point of the starting material when the reaction temperature is determined. The pressure for the acylation is not more than 10 kg/cm$^2$G, and in general, it is in the range between an atmospheric pressure and 5 kg/cm$^2$G. This pressure is determined according to the molar ratio of HF-BF$_3$ and the acylation temperature. Since the acylation reaction proceeds in a homogeneous liquid phase, no vigorous stirring is required.

In the present invention, the acylation reaction is carried out by any one of continuous, semi-continuous and batch methods. For example, in the semi-continuous method, at first, the acyl fluoride synthesis solution is introduced to a reactor, and then, the pressure inside the reactor is reduced. Thereafter, the acyl fluoride synthesis solution is allowed to absorb BF$_3$, and then, an aromatic compound is continuously introduced into the reactor to carry out the acylation reaction.

The reaction product obtained by the acylation reaction is a hydrogen fluoride solution of a complex of an aromatic acylation product and HF-BF$_3$. And, the bond between the aromatic acylation product and HF-BF$_3$ is decomposed by heating the HF solution, and HF and BF$_3$ can be separated. It is necessary to decompose the complex as smoothly as possible in order to avoid a thermal change of the product. In general, the thermal decomposition of the complex is smoothly carried out by subjecting the HF solution of the complex to distillation with a distillation column by using a solvent inert to HF-BF$_3$. Separated HF and BF$_3$ are preferably recycled. Specifically, the aromatic acylation product can be separated from HF and BF$_3$ according to the method described in U.S. Pat. No. 4,967,011. The above solvent inert to HF-BF$_3$ is selected from benzene, toluene and chlorobenzene, or also selected from mixtures of any one of these with pentane, hexane, cyclohexane, or the like, as described in the above U.S. Pat. No. 4,967,011. Separated HF is mainly recycled to the step of preparing the acyl fluoride synthesis solution.

As BF$_3$ for the acylation reaction, it is preferred to use BF$_3$ which is separated when the complex of an aromatic acylation product and HF-BF$_3$ from the acylation reactor is decomposed under heat (step d). This BF$_3$ may be directly introduced into the acylation reactor. However, BF$_3$ works as a catalyst to polymerize an unreacted olefin present in the acyl fluoride synthesis solution, and the reaction between the aromatic compound as a starting material and the olefin in the acylation reactor is limited as described above. Further, acyl fluoride and BF$_3$ form a complex to promote the acylation reaction, and as a result, the yield of the aromatic acylation product is improved. Therefore, the process of the present invention is provided with a step of forming a complex in which the acyl fluoride synthesis solution is brought into contact with BF$_3$, and then the resultant reaction mixture is fed to the acylation reactor.

As described above, the pressure for the acyl fluoride synthesis is not more than 100 kg/cm$^2$G, preferably 20 to 80 kg/cm$^2$G, and the pressure for the acylation reaction is not more than 10 kg/cm$^2$G. In the acylation step (step c), therefore, carbon monoxide dissolved in the acyl fluoride synthesis solution and nitrogen and hydrocarbon gas which are present in the starting materials are released, and BF$_3$ is taken out together with a gas of these. In the present invention, the acyl fluoride synthesis solution may be brought into contact with this gas. In this case, BF$_3$ being taken out together with the released gas is absorbed in the acyl fluoride synthesis solution, and therefore, the discharge of BF$_3$ works out of the reaction system is prevented. Further, the BF$_3$ works as a catalyst to polymerize an unreacted olefin present in the acyl fluoride synthesis solution, and the reaction between the aromatic compound as a starting material and the olefin is limited. As a result, the yield of the aromatic acylation product increases.

There may be used a combination of a BF$_3$ absorption tank in which the gas released in the acylation step (step c) is brought into contact with the acyl fluoride synthesis solution to allow the acyl fluoride synthesis solution to absorb BF$_3$ taken out together with the above released gas, with a complex preparation tank in which BF$_3$ separated in the step of separating the aromatic acylation product (step d) is absorbed in the acyl fluoride synthesis solution. In this case, the following is preferred to remove BF$_3$ completely. That is, at first, the acyl fluoride synthesis gas is brought into contact with the released gas in the BF$_3$ absorption tank, and then the acyl fluoride synthesis gas is allowed to absorb BF$_3$ separated in the step of separating the aromatic acylation product.

The method for the BF$_3$ absorption, that is, the method for bringing BF$_3$ separated in the step of separating the aromatic acylation product (step d) or the method for bringing the gas released in the acylation step into contact with the acyl fluoride synthesis solution is not specially limited. The released gas can be brought into contact with the acyl fluoride by a method in which a tank for the BF$_3$ absorption is provided before the acylation reactor and the released gas is blown into the acyl fluoride synthesis solution, by a method in which the tank for the BF$_3$ absorption is provided with a stirrer and the acyl fluoride synthesis solution and the released gas are together stirred, by a method in which the released gas is allowed to pass a packed column containing the acyl fluoride synthesis solution, and by some other methods. In addition, the discharge of BF$_3$ in the released gas out of the system can be also prevented by a method in which the released gas is brought into contact with the aromatic compound as a starting material, although this method is limited to a case where the aromatic compound is a liquid at a comparatively low temperature, e.g. toluene, xylene, etc.

The present invention will be described below by reference to drawing. FIG. 1 is a flow chart showing one embodiment in which an aromatic acylation product is produced according to the process of the present invention. An acyl fluoride synthesis reactor 4 is charged with an olefin as a starting material through a flow path 1, with carbon monoxide through a flow path 2 and with HF and BF$_3$ as a catalyst through a flow path 3. An acyl fluoride is synthesized. In addition, a solution of BF$_3$ in hydrogen fluoride, recovered in a distillation column, is used as the above catalyst. The resultant acyl fluoride synthesis solution is introduced into a BF$_3$ absorption tank 6 through a flow path 5, and brought into contact with a gas released in an acylation reactor 8 and introduced through a flow path 7. In the BF$_3$ absorption tank 6, BF$_3$ in the released gas is absorbed into the acyl fluoride synthesis solution, and carbon monoxide, nitrogen and hydrocarbon gas are purged through a flow path 9.

The acyl fluoride synthesis solution is introduced into a complex preparation tank 11 through a flow path 10 to be brought into contact with BF$_3$ introduced through a flow path 12, whereby a complex of acyl fluoride and HF-BF$_3$ is obtained. This BF$_3$ is that which is recovered from a distillation column. A solution from the complex preparation tank 11 is introduced into the acylation reactor 8 through a flow path 13. In the acylation reactor 8, the acyl fluoride is reacted with an aromatic compound introduced as a starting material through a flow path 14. A reaction solution containing the resultant complex of an aromatic acylation compound and HF-BF$_3$ is charged to a distillation column through a flow path 15 to separate the complex into the aromatic acylation compound as a product from HF and BF$_3$. Pumps are provided as required although no pump is described in FIG. 1.

When the acylation reaction is carried out after the absorption of BF$_3$ in the acyl fluoride synthesis solution according to the present invention, the amount of by-products can be remarkably reduced, and the intended acylation product can be obtained in high yields.

The process for producing an acylation product in the presence of HF-BF$_3$ as a catalyst according to the present invention has characteristic features in that the HF-BF$_3$ can be easily and completely recovered with simple procedures and recycled. Thus, the present invention industrially significant to a great extent.

Further, according to the present invention, BF$_3$ contained in a gas released from the acylation reactor can be effectively utilized to obviate any special means of environmental protection.

The present invention will be described further in detail hereinafter by reference to Examples, to which the present invention shall not be limited.

EXAMPLE 1

There was used a 500 cc stainless steel autoclave having a stirrer, three inlet nozzles in the top portion, one outlet nozzle in the bottom portion and a jacket with which the reaction temperature could be controlled.

At first, the autoclave was flushed with carbon monoxide, and then 110 g (5.5 moles) of HF was introduced. Then, 6.8 g (0.10 mole) of BF$_3$ was introduced from a measuring tank with stirring to allow HF to absorb BF$_3$. Thereafter, while the reaction temperature was set at 35° C., the pressure inside the autoclave was increased up to 20 kg/cm$^2$ G with carbon monoxide. While the above reaction temperature and pressure were maintained, 21.0 g (0.50 mole) of propylene was fed to a gas phase portion within the autoclave over about 60 minutes, and further, the resultant mixture was stirred for 10 minutes. The amount of CO absorbed from a CO measuring tank during the reaction was 0.375 mole.

Thereafter, the reaction mixture was cooled to −10° C., and unreacted CO was extracted. Then, 44.2 g (0.65 mole) of BF$_3$ was gradually introduced from a BF$_3$ measuring tank. After the introduction of BF$_3$, 0.38 mole of 2-methylnaphthalene was fed into the autoclave with a pump over about 30 minutes. While the resultant mixture was stirred, an acylation reaction of the 2-methylnaphthalene was carried out at a reaction temperature of 5° C. The reaction product was analyzed with a gas chromatography. Table 1 shows the operation conditions of the above reactors and the results.

COMPARATIVE EXAMPLE 1

The same 500 cc autoclave as that used in Example 1, a 100 cc BF$_3$ absorption tank and a 500 cc acylation reactor having a stirrer were used to carry out a continuous synthesis reaction.

At first, isobutyryl fluoride was synthesized in the 500 cc autoclave in the same manner as in Example 1, and then the resultant synthesis solution was introduced into the 100 cc BF$_3$ absorption tank to allow it to absorb BF$_3$. Thereafter, the resultant absorption solution was reacted with 2-methylnaphthalene in the acylation reactor.

The reaction product liquid in the acylation reactor was distilled to separate an acylation product, HF and BF$_3$. Table 1 shows the operation conditions of the above reactors and the results.

In addition, when the continuous reaction started, a solution of BF$_3$ in HF recovered from the distillation column was fed to the acyl fluoride reactor as an HF-BF$_3$ mixed liquid, and BF$_3$ recovered from the distillation column was fed to the complex preparation tank.

Since, however, the molar ratio of the acyl fluoride (isobutyryl fluoride) to 2-methylnaphthalene was greater than 1, unreacted acyl fluoride remained in the reaction product. Due to this, in a next step where HF-BF$_3$ was separated from the aromatic acylation product (by distillation), the acyl fluoride and benzene as a solvent reacted with each other to form acyl benzene (isobutyryl benzene) as a byproduct in an amount of 0.9% by weight based on propylene. The formation of the acyl benzene made it difficult to recover the unreacted acyl fluoride, and a loss of the solvent occurred.

EXAMPLE 2

In the same continuous synthesis reaction as that in Example 1, the reaction was carried out by increasing the amount of 2-methylnaphthalene based on the acylation synthesis solution. The reaction mixture in the acylation reactor was distilled in the same manner as in Comparative Example 1. Since no acyl fluoride was present in the reaction mixture, no loss in the solvent was observed. Further, unreacted 2-methylnaphthalene was easily separated by distillation and recycled. Table 1 shows the operation conditions of the reactors and the results.

COMPARATIVE EXAMPLE 2

In the same continuous synthesis reaction as that in Comparative Example 1, the acylation reaction was carried out while BF$_3$ and 2-methylnaphthalene were simultaneously fed to the acylation reactor. Table 1 shows the operation conditions of the reactors and the results.

COMPARATIVE EXAMPLE 3

In the same continuous synthesis reaction as that in Comparative Example 2, the reaction was carried out by increasing the amounts of the catalyst and starting materials and the BF$_3$ absorption amount based on 2-methylnaphthalene. Table 1 shows the operation conditions of the reactors and the results.

TABLE 1

| Reaction method | Ex. 1 semi-continuous | CEx. 1 continuous | Ex. 2 continuous | CEx. 2 continuous | CEx. 3 continuous |
| --- | --- | --- | --- | --- | --- |
| (Acyl fluoride synthesis reaction) | | | | | |
| HF g/h (mol/h) | 110 (5.5) | 122 (6.1) | 108 (5.4) | 112 (5.6) | 154 (7.7) |
| BF$_3$ | 6.8 (0.10) | 5.4 (0.08) | 6.1 (0.09) | 4.8 (0.07) | 6.3 (0.09) |
| Propylene | 21.0 (0.50) | 19.7 (0.47) | 19.7 (0.47) | 18.5 (0.44) | 24.8 (0.59) |
| CO | 10.5 (0.378) | 9.9 (0.354) | 10.0 (0.356) | 8.9 (0.319) | 12.5 (0.488) |
| Pressure kg/cm$^2$ G | 20 | 20 | 20 | 20 | 20 |
| Temperature °C. | 35 | 35 | 35 | 35 | 35 |
| (Acylation reaction) | | | | | |
| 2-MN g/h (mol/h) | 54.0 (0.38) | 49.7 (0.35) | 56.8 (0.40) | 55.4 (0.39) | 72.4 (0.51) |
| BF$_3$ | 44.2 (0.65) | 50.0 (0.74) | 57.1 (0.84) | 39.8 (0.59) | 62.6 (0.92) |
| Pressure kg/cm$^2$ | 4 | 3.8 | 3.8 | 3.8 | 3.8 |
| Temperature °C. | 5 | 5 | 5 | 5 | 5 |
| (Reaction results) | | | | | |
| By-product/BMN wt. % | 0.27 | 0.76 | 1.29 | 10.6 | 7.6 |
| 2,6-BNM selectivity % | 90.6 | 91.2 | 92.2 | 68.8 | 85.4 |
| BMN/propylene mole % | 72.3 | 71.4 | 72.5 | 57.3 | 62.4 |

Notes:
By-product = isopropylmethylnaphthalenes
2-MN = 2-methylnaphthalene
BMN = acylation product (isobutyrylmethylnaphthalene)
2,6-BMN selectivity = content of 2,6-BMN inb BMN product

EXAMPLE 3

Example 1 was repeated except that the 2-methylnaphthalene as an aromatic compound was replaced with m-xylene, whereby 1-isobutyryl-2,4-dimethylbenzene was synthesized.

COMPARATIVE EXAMPLE 4

In the same semi-continuous synthesis reaction as that in Example 3, $BF_3$ and m-xylene were simultaneously fed to a isobutyryl fluoride synthesis solution to carry out an acylation reaction.

Table 2 shows the main reaction conditions and results of Example 3 and Comparative Example 4

TABLE 2

| Reation method | Ex. 3 semi-continouus | CEx. 4 semi-continuous |
| --- | --- | --- |
| (Acyl fluoride synthesis reaction) | | |
| HF g/h (mol/h) | 132 (6.6) | 156 (7.8) |
| $BF_3$ | 6.8 (0.1) | 8.2 (0.12) |
| Propylene | 25.2 (0.60) | 27.3 (0.65) |
| CO | 12.3 (0.439) | 13.4 (0.479) |
| Pressure kg/cm² G | 20 | 20 |
| Temperature °C. | 35 | 35 |
| (Acylation reaction) | | |
| MX g/h (mol/h) | 46.6 (0.44) | 50.9 (0.48) |
| $BF_3$ | 62.5 (0.92) | 79.6 (1.17) |
| Pressure kg/cm² | 4 | 4 |
| Temperature °C. | 5 | 5 |
| (Reaction results) | | |
| By-product/BDMB wt. % | 2.20 | 11.3 |
| 1,2,4-BDMB selectivity % | 98.7 | 97.3 |
| BDMB/propylene mole % | 69.5 | 56.7 |

Notes:
By-product = isopropyldimethylbenzenes
MX = m-xylene
BDMB = acylation product (isobutyryldimethylbenzene)
1,2,4-BDMB selectivity = content of 1,2,4-BDMB in BDMD product

EXAMPLE 4

A continuous reaction was carried out with the same 500 cc stainless steel autoclaves as that used in Comparative Example 1 as an acyl fluoride synthesis reactor and an acylation reactor 200 cc stainless steel autoclaves as a $BF_3$ absorption tank and a complex preparation tank.

The acyl fluoride synthesis reactor was flushed with carbon monoxide, and a $BF_3$/HF mixed liquid having a $BF_3$/HF molar ratio of 0.017 was introduced into the acyl fluoride synthesis reactor. When a continuous reaction started, a solution of $BF_3$ in HF recovered from a distillation column was used as a $BF_3$/HF mixed liquid.

Then, while the $BF_3$/HF was stirred at a reaction temperature of 35° C., the pressure inside the acyl fluoride synthesis reactor was increased up to 20 kg/cm²G with carbon monoxide. While these reaction temperature and pressure were maintained, 114.1 g/h of a $BF_3$/HF mixed liquid and 19.7 g/h of propylene were continuously introduced into a gas phase portion of the acyl fluoride synthesis reactor to synthesize isobutyryl fluoride. The synthesis solution containing the resultant isobutyryl fluoride was consecutively introduced into the $BF_3$ absorption tank, the complex preparation tank and the acylation reactor as shown in the flow chart of FIG. 1.

In the $BF_3$ absorption tank, the isobutyryl fluoride solution absorbed $BF_3$ contained in gas released from the acylation reactor, and no $BF_3$ was detected in the analysis of gas purged from the $BF_3$ absorption tank. In the complex preparation tank, the isobutyryl fluoride synthesis solution from the $BF_3$ absorption tank further absorbed $BF_3$ recovered from the distillation column, and in the acylation reactor, the resultant isobutyryl fluoride synthesis solution reacted with 2-methylnaphthalene to give 2-isobutyryl-6-methylnaphthalene.

Table 3 shows the operation conditions for the above tanks and reactors and results of the above reactions.

COMPARATIVE EXAMPLE 5

The procedures of Example 4 were repeated under the operation conditions shown in Table 3 except that an isobutyryl fluoride synthesis solution and $BF_3$ were directly introduced into the acylation reactor without using the $BF_3$ absorption tank and the complex preparation tank. Table 3 shows the results. The analysis of gas discharged from the acylation reactor showed that the gas contained 0.035 mol/h of $BF_3$, which corresponded to 3.6 mole % of $BF_3$ introduced into the acylation reactor.

EXAMPLE 5

The procedures of Example 4 were repeated under the operation conditions shown in Table 3 except that the 2-methylnaphthalene as an aromatic compound was replaced with 2-ethylnaphthalene, whereby 2-isobutyryl-6-ethylnaphthalene was synthesized. Table 3 shows the results. In the analysis of gas purged from the $BF_3$ absorption tank, no $BF_3$ was detected.

EXAMPLE 6

The procedures of Example 4 were repeated under the operation conditions shown in Table 3 except that the 2-methylnaphthalene as an aromatic compound was replaced with m-xylene, whereby 1-isobutyryl-2,4-dimethylbenzene was synthesized. Table 3 shows the results. In the analysis of gas purged from the $BF_3$ absorption tank, no $BF_3$ was detected.

EXAMPLE 7

The procedures of Example 4 were repeated under the operation conditions shown in Table 3 except that the propylene was replaced with 1-butene and that the 2-methylnaphthalene was replaced with toluene, whereby 2,4'-dimethylbutyrophenone was synthesized. Table 3 shows the results. In the analysis of gas purged from the $BF_3$ absorption tank, no $BF_3$ was detected.

COMPARATIVE EXAMPLE 6

The procedures of Example 7 were repeated under the operation conditions shown in Table 3 except that an acyl fluoride synthesis liquid and $BF_3$ were directly introduced into the acylation reactor without using the $BF_3$ absorption tank and the complex preparation tank. Table 3 shows the results. The analysis of gas discharged from the acylation reactor showed that the gas contained 0.020 mol/h of $BF_3$, which corresponded to 2.5 mole % of $BF_3$ introduced into the acylation reactor.

TABLE 3

| | Ex. 4 | CEx. 5 | Ex. 5 | Ex. 6 | Ex. 7 | CEx. 6 |
| --- | --- | --- | --- | --- | --- | --- |
| Acyl fluoride synthesis reactor | | | | | | |

TABLE 3-continued

|  | Ex. 4 | CEx. 5 | Ex. 5 | Ex. 6 | Ex. 7 | CEx. 6 |
| --- | --- | --- | --- | --- | --- | --- |
| HF, mol/h | 5.40 | 5.40 | 5.40 | 5.40 | 5.40 | 5.40 |
| $BF_3$, mol/h | 0.09 | 0.09 | 0.09 | 0.09 | 0.09 | 0.09 |
| Olefin, mol/h | 0.47 | 0.47 | 0.48 | 0.47 | 0.47 | 0.47 |
| CO, mol/h | 0.357 | 0.357 | 0.364 | 0.357 | 0.343 | 0.343 |
| Pressure, $kg/cm^2$ G | 20 | 20 | 20 | 20 | 20 | 20 |
| Temperature, °C. | 35 | 35 | 35 | 35 | 35 | 35 |
| $BF_3$ absorption tank |  |  |  |  |  |  |
| Pressure, $kg/cm^2$ G | 3.5 | — | 3.5 | 3.5 | 3.5 | — |
| Temperature, °C. | −20 | — | −20 | −20 | −20 | — |
| Complex preparation tank |  |  |  |  |  |  |
| $BF_3$, mol/h | 0.84 | — | 0.858 | 0.82 | 0.686 | — |
| Pressure, $kg/cm^2$ G | 3.7 | — | 3.7 | 3.7 | 3.7 | — |
| Temperature, °C. | −25 | — | −25 | −25 | −25 | — |
| Acylation reactor |  |  |  |  |  |  |
| Aromatic compound, mol/h | 0.40 | 0.40 | 0.40 | 0.39 | 0.412 | 0.412 |
| $BF_3$ | — | 0.875 | — | — | — | 0.706 |
| Pressure, $kg/cm^2$ G | 3.6 | 3.6 | 3.6 | 3.6 | 3.6 | 3.6 |
| Temperature, °C. | −10 | −10 | −10 | −10 | −10 | −10 |
| Reaction results |  |  |  |  |  |  |
| By-product/acylation product, wt. % | 1.20 | 10.3 | 1.24 | 2.00 | 1.02 | 9.82 |
| Selectivity, % | 93.1 | 70.2 | 94.2 | 98.8 | 97.4 | 95.8 |
| Acylation product/olefin, % | 73.0 | 58.4 | 72.8 | 71.2 | 71.2 | 56.5 |

Notes: Names of olefins, aromatic compounds, by-products and acylation products.

|  | Olefin | Aromatic compound | By-product | Acylation (selectivity) product |
| --- | --- | --- | --- | --- |
| Ex. 4, CEx. 5 | propylene | 2-methyl-naphthalene | isopropylmethyl-naphthalene | isobutyrylmethyl-naphthalene (2,6-form) |
| Ex. 5 | propylene | 2-ethyl-naphthalene | isopropylethyl-naphthalene | isobutyrylethyl-naphthalene (2,6-form) |
| Ex. 6 | propylene | m-xylene | isopropyl-dimethylbenzene | isobutyldimethyl-benzene (1,2,4-form) |
| Ex. 7, CEx. 6 | 1-butene | toluene | butylmethyl-benzene | dimethylbutyro-phenone (2,4'-form) |

What is claimed is:

1. A process for producing an aromatic acylation product from an aromatic compound, an olefin and carbon monoxide, which comprises the steps of:
    (a) reacting an olefin with carbon monoxide in the presence of hydrogen fluoride and boron trifluoride at a pressure of not more than 100 $kg/cm^2G$ to prepare an acyl fluoride synthesis solution,
    (b) allowing the acyl fluoride synthesis solution to absorb boron trifluoride to form a complex of acyl fluoride and boron trifluoride,
    (c) subjecting an aromatic compound to an acylation reaction with a reaction mixture containing the complex of acyl fluoride and boron trifluoride, obtained in the step (b), to form a complex of boron trifluoride, hydrogen fluoride and an aromatic acylation compound, provided that the amount of the acyl fluoride in the complex of acyl fluoride and boron trifluoride is less than 1 mole per mole of the aromatic compound, and
    (d) separating the aromatic acylation compound from the complex formed in the step (c) by heating a reaction mixture obtained in the step (c).

2. A process according to claim 1, wherein the step (c) has a step of releasing gas containing boron trifluoride.

3. A process according to claim 2, wherein the gas released is used as boron trifluoride to be absorbed in the acyl fluoride synthesis liquid.

4. A process according to claim 2, wherein the gas released is absorbed in the aromatic compound before the acylation reaction.

5. A process according to claim 1, wherein the step (d) is carried out by distillation in the presence of a solvent inert to hydrogen fluoride and boron trifluoride.

6. A process according to claim 1, wherein the boron trifluoride from the step (d) is absorbed in the acyl fluoride synthesis liquid.

7. A process according to claim 1, wherein the boron trifluoride from the step (d) added into the acylation reaction.

8. A process according to claim 1, wherein the aromatic compound is at least one compound selected from alkylbenzene compounds, alkylnaphthalene compounds, phenolic compounds, naphthol compounds and aromatic ether compounds.

9. A process according to claim 1, wherein the olefin has 2 to 5 carbon atoms.

10. A process according to claim 1, wherein the hydrogen fluoride is used in an amount of 5 to 20 moles per mole of the olefin.

11. A process according to claim 1, wherein the boron trifluoride is used in the step (a) in an amount of 0.001 to 0.03 mole per mole of the hydrogen fluoride.

12. A process according to claim 1, wherein the acyl fluoride is used in an amount of 0.8 to less than 1.0 mole per mole of the aromatic compound.

13. A process according to claim 1, wherein the boron trifluoride is used in the step (c) in an amount of 1.5 to 3 moles per mole of the aromatic compound.

14. A process according to claim 1, wherein the hydrogen fluoride is used in the step (c) in an amount of 5 to 20 moles per mole of the aromatic compound.

* * * * *